US012806060B2

(12) United States Patent
Mckenzie

(10) Patent No.: US 12,806,060 B2
(45) Date of Patent: Nov. 24, 2026

(54) ORAL COMMISSURAL SPLINT

(71) Applicant: Kenzie Therapeutics LLC, Mesa, AZ (US)

(72) Inventor: Charles Mckenzie, Mesa, AZ (US)

(73) Assignee: Kenzie Therapeutics LLC, Mesa, AZ (US)

( * ) Notice: Subject to any disclaimer, the term of this patent is extended or adjusted under 35 U.S.C. 154(b) by 0 days.

(21) Appl. No.: 19/182,370

(22) Filed: Apr. 17, 2025

(65) Prior Publication Data

US 2026/0124059 A1 May 7, 2026

Related U.S. Application Data

(60) Provisional application No. 63/638,604, filed on Apr. 25, 2024.

(51) Int. Cl.
*A61F 5/042* (2006.01)

(52) U.S. Cl.
CPC .................................... *A61F 5/042* (2013.01)

(58) Field of Classification Search
CPC ........... A61C 9/0006; A61C 7/08; A61C 7/36; A61F 5/56–566; A63B 71/085; A63B 2071/086; A63B 2071/088; Y10S 602/902; A61B 90/16
See application file for complete search history.

(56) References Cited

U.S. PATENT DOCUMENTS

| | | | | |
|---|---|---|---|---|
| 3,878,610 A * | 4/1975 | Coscina | ............... | A61C 9/0006 433/37 |
| 2013/0066236 A1* | 3/2013 | Herman | ............... | A63B 71/085 600/595 |
| 2024/0065814 A1* | 2/2024 | Quartey | ............... | A61C 9/0006 |

* cited by examiner

*Primary Examiner* — Alireza Nia
*Assistant Examiner* — Robin Han
(74) *Attorney, Agent, or Firm* — Kenneth C. Booth; Booth Udall, PLC.

(57) ABSTRACT

An oral commissural splint with a mouthguard tray removably mounted on teeth of a patient. The platform includes a textured upper surface, a front wall with a ridge, a plurality of openings spaced along the lower edge of the front wall, and a rear wall extending up from the tooth platform opposite the front wall. Two commissural supports securely couple to the mouthguard tray, each including a clip to engage the ridge of the mouthguard tray and insert into the openings of the mouthguard tray, and a body configured for long-term support of a commissure at a corner of the mouth of the patient when the commissural support is coupled to the mouthguard tray and inserted into the mouth of the patient. Each clip is removably attached at a desired position on the mouthguard tray.

18 Claims, 8 Drawing Sheets

ORAL COMMISSURAL SPLINT

RELATED APPLICATIONS

This application claims the benefit of U.S. provisional patent application 63/638,604, filed 25 Apr., 2024 to Charles Mckenzie, titled "Oral Commissural Splint," the entirety of the disclosure of which is hereby incorporated by this reference.

TECHNICAL FIELD

This document relates to dental devices, and more specifically to an oral commissural splint designed to support and stabilize the oral commissure, particularly in patients undergoing various dental or medical treatments that impact the structure or function of the oral cavity.

BACKGROUND

Oral commissure are the corner points of the mouth where the upper and lower lips meet. Various medical and dental conditions, particularly associated with injuries to these areas, such as cuts and electrical burns, can affect the stability and integrity of the oral commissure, leading to complications involving alterations in speaking, eating and mandibular motion, thereby significantly impacting a patient's quality of life. Prosthetic treatment of such injuries involves providing a device to apply physical resistance to scar contracture to maintain the oral commissures in their normal relationship through a splint.

Existing devices aimed at supporting the mouth and lips post injury, called oral commissural splints, typically include various structures that attempt to maintain the integrity and position of the mouth's corners. However, a significant limitation of these existing solutions is their lack of adjustability and specificity in application. Because each patient's mouth is different and has a different size and post-injury spacing, and the needed spacing necessarily changes throughout different stages of recovery, one-size-fits-all designs are ineffective for most patients, and custom splints are needed to accommodate individual anatomical differences among patients. Use of an incorrectly sized splint can lead to inadequate support, discomfort, and even aggravation of existing conditions due to poor fit.

Creation of an oral commissural splint typically involves taking a mold of the patient's mouth and creating a custom-sized and spaced oral commissure through use of an acrylic palatal surface with two commissural posts to hold the corners of the mouth in the desired, open position. Other splints use acrylic splints with elastics, prong prosthesis or acrylic hooks. If teeth are available, the splint is made to fit over, or be cemented to, the maxillary dentition. However, creating custom splints is uncomfortable when taking the molds and takes time to create. In addition, the splint needs to be recreated as therapy continues when the patient's treatment situation changes.

SUMMARY

The present disclosure relates to an oral commissural splint, comprising a mouthguard tray configured to be inserted into a mouth of a patient and removably mounted on teeth of the patient, the mouthguard tray having: a tooth platform having an upper surface with a plurality of textured structures on the upper surface; a front wall extending up from the tooth platform and having an upper edge defining a ridge and a lower edge having a plurality of openings spaced along the lower edge of the front wall; and a rear wall extending up from the tooth platform opposite the front wall; and two commissural supports configured to securely couple to the mouthguard tray, each of the two commissural supports having: a clip having a lip configured to engage the ridge of the mouthguard tray and at least one clip arm having a clip projection configured to insert into each of the plurality of openings of the mouthguard tray, wherein the lip and the at least one clip arm together are configured to hold the clip to the mouthguard tray; and a body integral with and extending away from the clip, the body configured for long-term support of a commissure at a corner of the mouth of the patient when the commissural support is coupled to the mouthguard tray and the mouthguard tray is inserted into the mouth of the patient and removably mounted on the teeth of the patient; wherein each clip of the two commissural supports is configured to removably snap into a desired position on the mouthguard tray with the lip engaged with the ridge of the mouthguard tray and the clip projection of the at least one clip arm inserted into at least one of the plurality of openings.

Particular embodiments of the disclosure may include one or more of the following features. The plurality of textured structures may be configured to mechanically engage a mold within the mouthguard tray, the mold formed of a dental impression material. Positions of the two commissural supports with respect to the mouthguard tray may be adjustable. A position of a first commissural support of the two commissural supports with respect to the mouthguard tray is independent of a position of a second commissural support of the two commissural supports with respect to the mouthguard tray. The first commissural support and the second commissural support are positionable such that the position of the first commissural support is closer to a center of the mouthguard tray than the position of the second commissural support.

Aspects of the disclosure relate to an oral commissural splint, comprising a mouthguard tray configured to be removably retained within a mouth of a patient, the mouthguard tray having a front wall, the front wall having a plurality of openings spaced along a lower edge of the front wall, and at least one commissural support configured to securely couple to the mouthguard tray, the at least one commissural support having a clip with at least one clip arm configured to hold the clip to the mouthguard tray and a body extending away from the clip, the body configured for long-term support of a commissure at a corner of the mouth of the patient when the at least one commissural support is coupled to the mouthguard tray and the mouthguard tray is inserted into the mouth of the patient, wherein the clip of the at least one commissural support is configured to removably snap into a desired position on the mouthguard tray with the at least one clip arm inserted into at least one of the plurality of openings of the mouthguard tray.

Particular embodiments of the disclosure may include one or more of the following features. The mouthguard tray further having a tooth platform having an upper surface with a plurality of textured structures on the upper surface, wherein the front wall extends up from the tooth platform and wherein the plurality of textured structures are configured to mechanically engage a mold within the mouthguard tray, the mold formed of a dental impression material. The front wall having an upper edge defining a ridge and the clip having a lip configured to engage the ridge, wherein the clip of the at least one commissural support is configured to removably snap into the desired position on the mouthguard tray with the lip engaged with the ridge of the mouthguard tray and the at least one clip arm inserted into at least one of the plurality of openings of the mouthguard tray. A position of a first commissural support of the at least one commissural support with respect to the mouthguard tray is independent of a position of a second commissural support of the at least one commissural support with respect to the mouthguard tray. The first commissural support and the second commissural support are positionable such that the position of the first commissural support is closer to a center of the mouthguard tray than the position of the second commissural support.

Aspects of the disclosure relate to an oral commissural splint, comprising a mouthguard tray configured to be removably retained within a mouth of a patient, and at least one commissural support configured to removably snap into a desired position on the mouthguard tray and support a commissure at a corner of the mouth of the patient when the mouthguard tray is inserted into the mouth of the patient.

Particular embodiments of the disclosure may include one or more of the following features. The mouthguard tray having a front wall, the front wall having a plurality of openings spaced along a lower edge of the front wall. The at least one commissural support having a clip with at least one clip arm configured to hold the clip to the mouthguard tray and a body extending away from the clip, the body configured to support the commissure at the corner of the mouth of the patient when the mouthguard tray is inserted into the mouth of the patient. The at least one commissural support is configured to removably snap into the desired position on the mouthguard tray with the at least one clip arm inserted into an opening of the plurality of openings of the mouthguard tray. The front wall having an upper edge defining a ridge and the clip having lip configured to engage the ridge, wherein the clip of the at least one commissural support is configured to removably snap into the desired position on the mouthguard tray with the lip engaged with the ridge of the mouthguard tray and the at least one clip arm inserted into at least one of the plurality of openings of the mouthguard tray. The body is integral with the clip. The mouthguard tray further having a tooth platform having an upper surface with a plurality of textured structures on the upper surface, wherein the plurality of textured structures are configured to mechanically engage a mold within the mouthguard tray, the mold formed of a dental impression material. A position of the at least one commissural support with respect to the mouthguard tray is adjustable. A position of a first commissural support of the at least one commissural support with respect to the mouthguard tray is independent of a position of a second commissural support of the at least one commissural support with respect to the mouthguard tray. The first commissural support and the second commissural support are positionable such that the position of the first commissural support is closer to a center of the mouthguard tray than the position of the second commissural support.

The foregoing and other aspects, features, and advantages will be apparent from the DESCRIPTION and DRAWINGS, and from the CLAIMS if any are included.

BRIEF DESCRIPTION OF THE DRAWINGS

Implementations will hereinafter be described in conjunction with the appended and/or included DRAWINGS, where like designations denote like elements.

DETAILED DESCRIPTION

Figure 1:
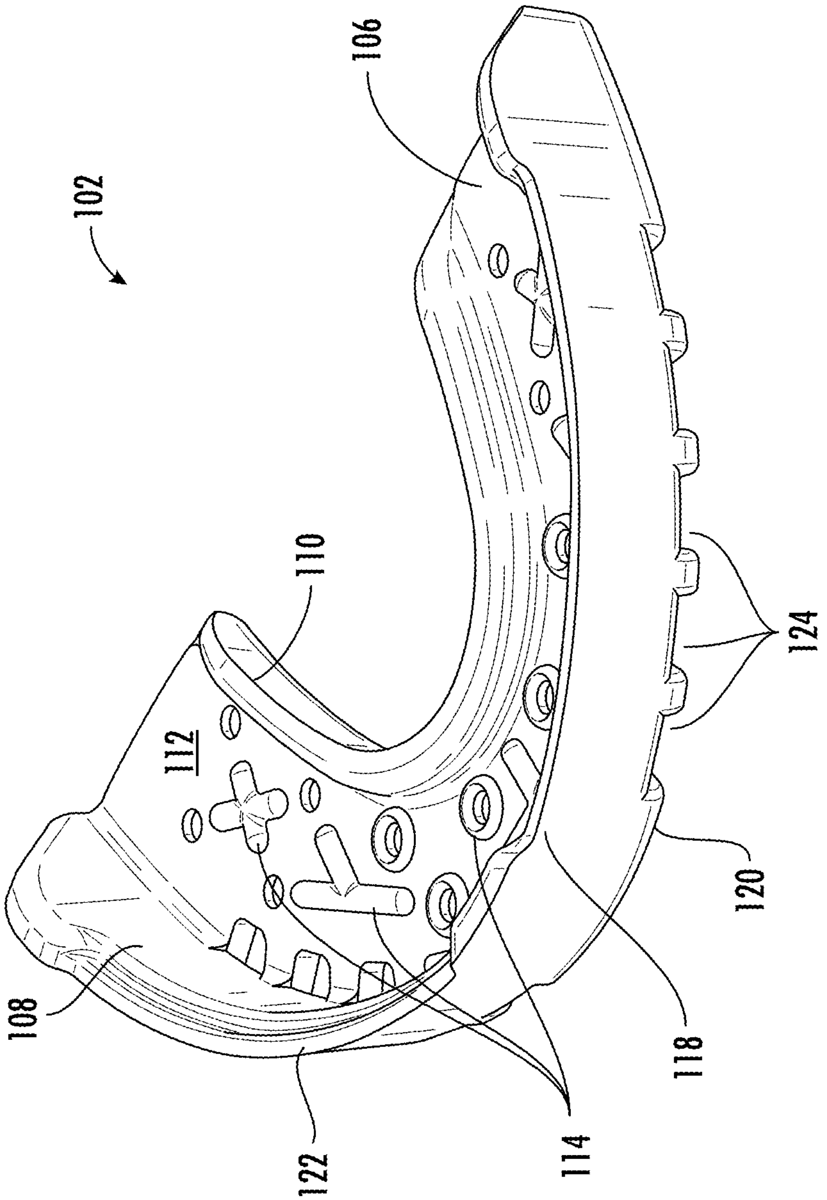
FIG. 1 is a perspective view of a mouthguard tray of an oral commissural splint according to some embodiments.
Figure 2:
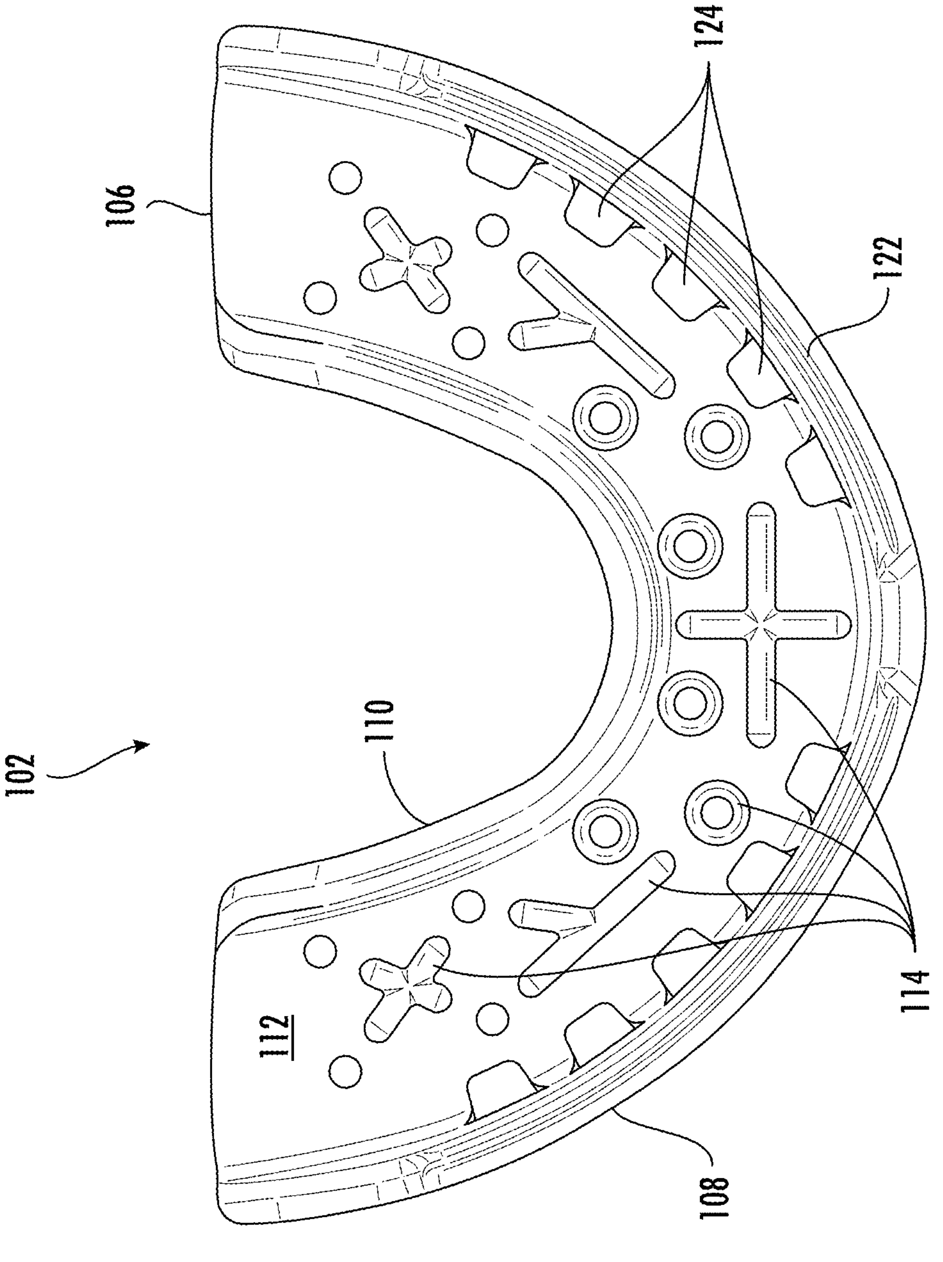
FIG. 2 is a top view of a mouthguard tray of an oral commissural splint according to some embodiments.
Figure 3:
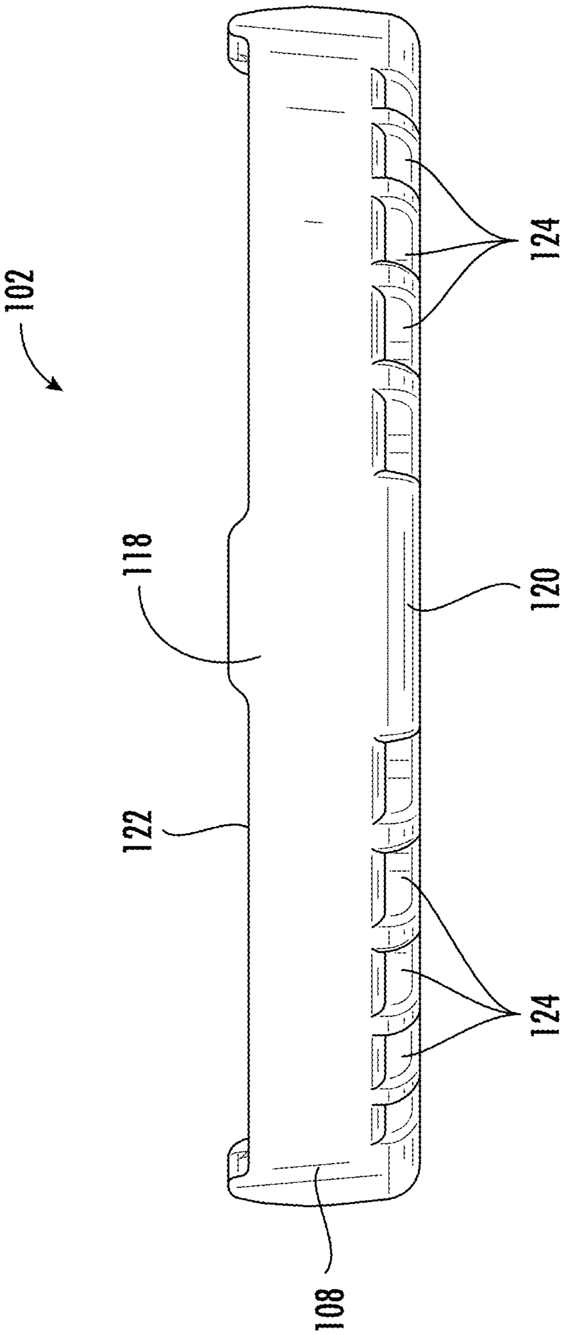
FIG. 3 is a front view of a mouthguard tray of an oral commissural splint according to some embodiments.
Figure 4:
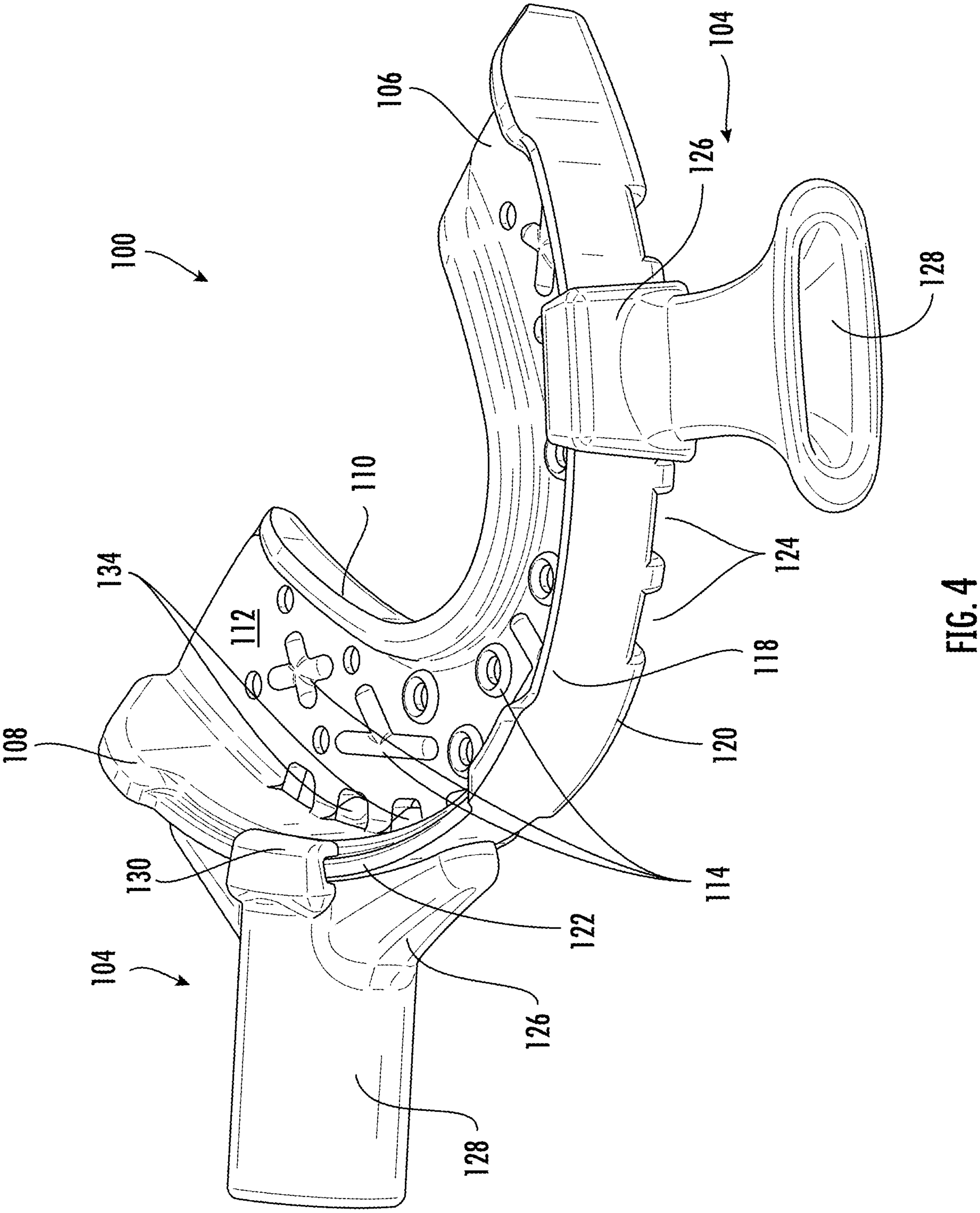
FIG. 4 is a perspective view of an oral commissural splint according to some embodiments.
Figure 5:
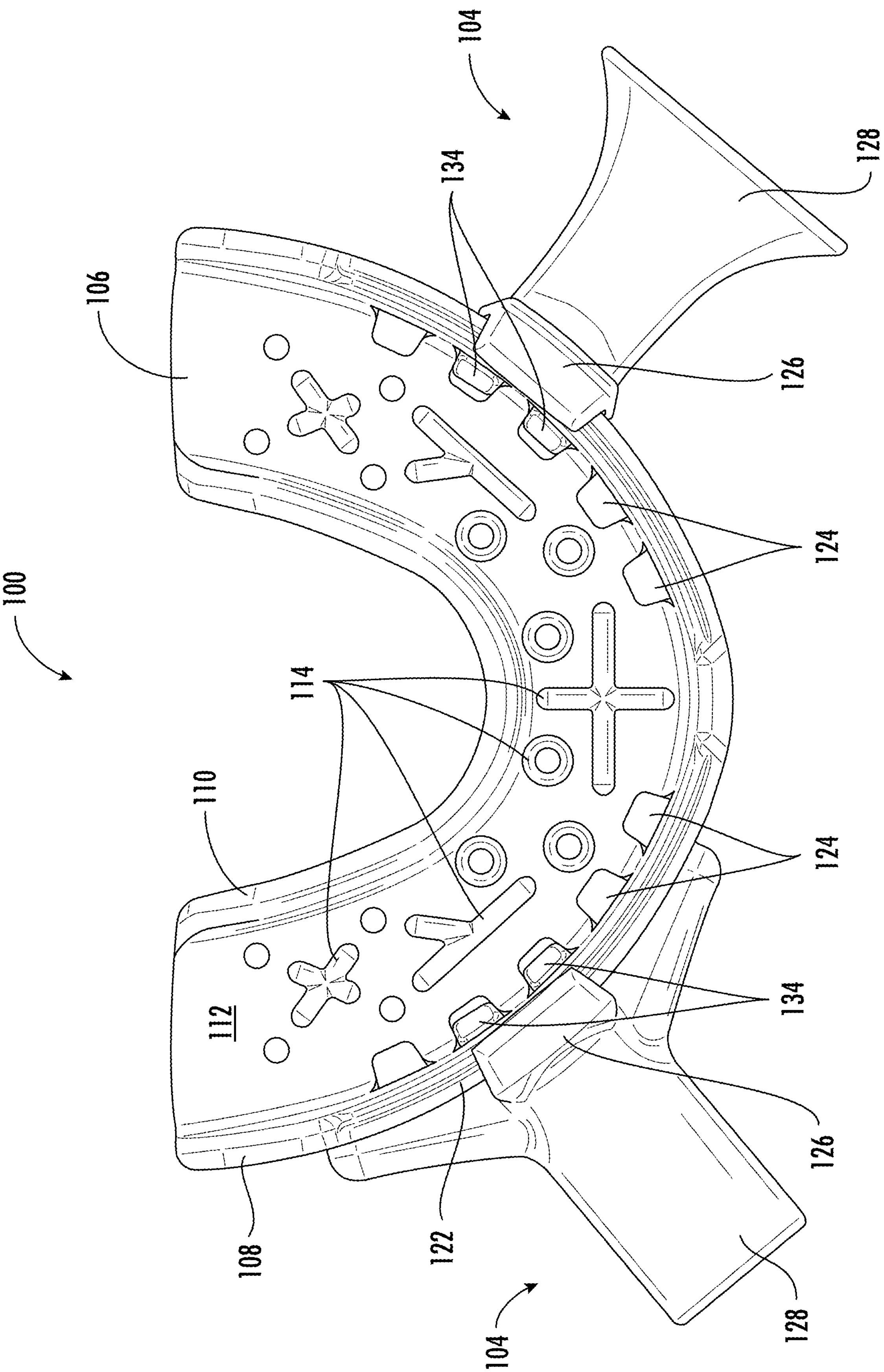
FIG. 5 is a top view of an oral commissural splint according to some embodiments.

Detailed aspects and applications of the disclosure are described below in the following drawings and detailed description of the technology. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the disclosure. It will be understood, however, by those skilled in the relevant arts, that embodiments of the technology disclosed herein may be practiced without these specific details. It should be noted that there are many different and alternative configurations, devices and technologies to which the disclosed technologies may be applied. The full scope of the technology disclosed herein is not limited to the examples that are described below.

The singular forms "a," "an," and "the" include plural referents unless the context clearly dictates otherwise. Thus, for example, reference to "a step" includes reference to one or more of such steps.

The word "exemplary," "example," or various forms thereof are used herein to mean serving as an example, instance, or illustration. Any aspect or design described herein as "exemplary" or as an "example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented, but have been omitted for purposes of brevity.

Throughout the description and claims of this specification, the words "comprise" and "contain" and variations of the words, for example "comprising" and "comprises", mean "including but not limited to", and are not intended to (and do not) exclude other components.

As required, detailed embodiments of the present disclosure are included herein. It is to be understood that the disclosed embodiments are merely exemplary of the invention that may be embodied in various forms. Therefore, specific structural and functional details disclosed herein are not to be interpreted as limits, but merely as a basis for teaching one skilled in the art to employ the present invention. The specific examples below will enable the disclosure to be better understood. However, they are given merely by way of guidance and do not imply any limitation.

The present disclosure may be understood more readily by reference to the following detailed description taken in connection with the accompanying figures and examples, which form a part of this disclosure. It is to be understood that this disclosure is not limited to the specific materials, devices, methods, applications, conditions, or parameters described and/or shown herein, and that the terminology used herein is for the purpose of describing particular embodiments by way of example only and is not intended to be limiting of the claimed inventions. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

More specifically, this disclosure, its aspects and embodiments, are not limited to the specific material types, components, methods, or other examples disclosed herein. Many additional material types, components, methods, and procedures known in the art are contemplated for use with particular implementations from this disclosure. Accordingly, for example, although particular implementations are disclosed, such implementations and implementing components may comprise any components, models, types, materials, versions, quantities, and/or the like as is known in the art for such systems and implementing components, consistent with the intended operation.

The present disclosure is related to an oral commissural splint that is configured to allow for rapid adjustment such that the same splint can be used to meet the evolving needs of a patient over the course of the patient's treatment. In addition, the presently disclosed oral commissural splint allows for adjustment of each commissural support independent of the position of the other commissural supports. Thus, the presently disclosed oral commissural splint provides a benefit over conventional oral commissural splints because there is no need for a redesign or recreation of the oral commissural splint over time. Instead, the presently disclosed oral commissural splint has commissural supports which can be easily adjusted to the desired positions to support the patient's commissure where currently needed, including if the patient requires different positions for each commissure.

The present disclosure is related to an oral commissural splint 100, an embodiment of which is shown in FIGS. 1-7. In some embodiments, the oral commissural splint 100 comprises a mouthguard tray 102 and a commissural support 104. The mouthguard tray 102 is configured to be removably retained in the mouth of the patient, such as by mounting onto the teeth of the patient. The commissural support 104 is configured to couple to the mouthguard tray 102 in a desired position on the mouthguard tray 102 and is configured to support the commissure at the corner of the mouth of the patient when the mouthguard tray 102 is inserted into the mouth of the patient. In some embodiments, the commissural support 104 is configured to snap into the desired position, as will be described in more detail below.

Figure 7:
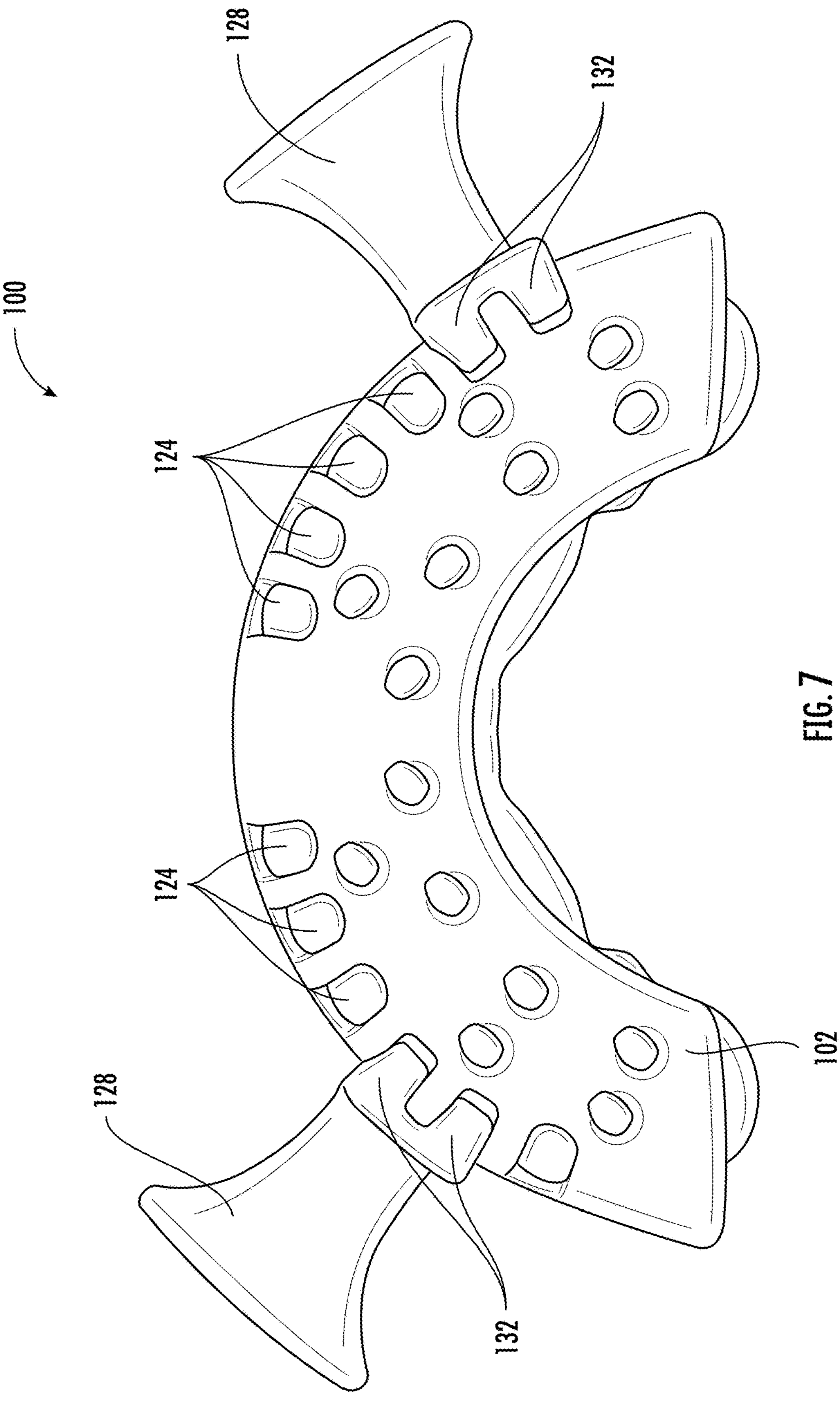
FIG. 7 is a bottom view of an oral commissural splint according to some embodiments with a mold retained in the mouthguard tray.
Figure 8:
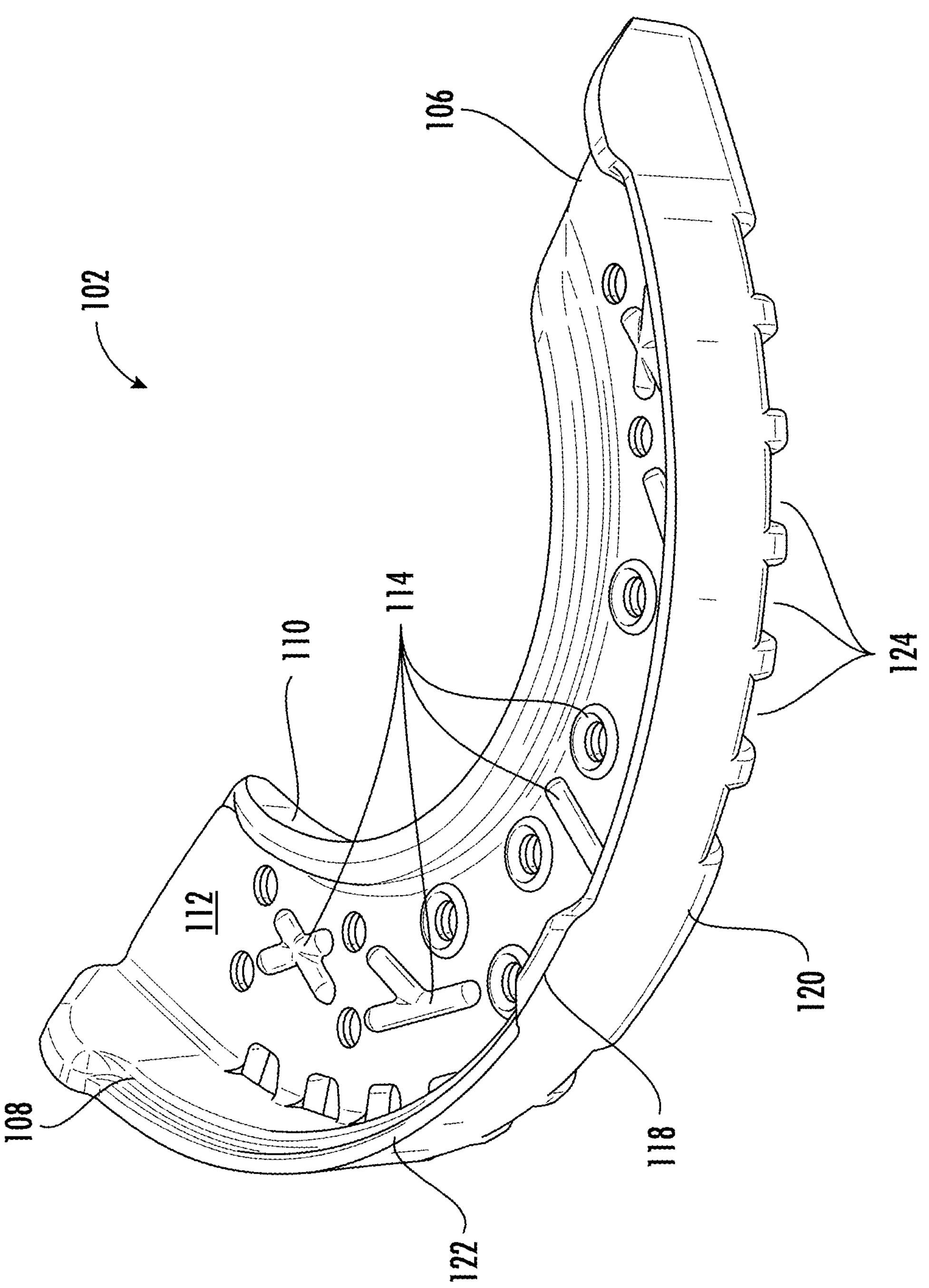
FIG. 8 is a perspective view of a mouthguard tray of an oral commissural splint according to some embodiments.

In some embodiments, the mouthguard tray 102 has a tooth platform 106, a front wall 108, and/or a rear wall 110. The mouthguard tray 102 may have a curved shape. In some embodiments, the curved shape of the mouthguard tray 102 is configured to follow the curve of the patient's teeth. Thus, the mouthguard tray 102 may be smaller or larger depending on the size of the patient's mouth and the curve of their teeth. FIGS. 1 and 8 illustrate two different sizes of mouthguard tray 102. The tooth platform 106 is bounded on one side by the front wall 108 and on the other side by the rear wall 110. In some embodiments, the tooth platform 106 has an upper surface 112 with a plurality of textured structures 114 on the upper surface 112. These textured structures 114 may be configured to mechanically engage a mold 116 within the mouthguard tray 102 (see FIGS. 6 and 7). The mold 116 may be formed of a dental impression material. The mold 116 allows the oral commissural splint 100 to be fitted specifically to the patient's teeth and thus retained in the patient's mouth. When first fitted into the mouthguard tray 102, the mold 116 is malleable and fills in the spaces between the plurality of textured structures 114. This helps to prevent movement between the mold 116 and the mouthguard tray 102 and therefore allows the commissural support 104 to be positioned exactly in the desired position with respect to the patient's mouth.

The front wall 108 extends up from the tooth platform 106 and the rear wall 110 extends up from the tooth platform 106 opposite the front wall 108. The front wall 108 has an upper edge 118 and a lower edge 120. In some embodiments, the upper edge 118 defines a ridge 122. In some embodiments, the lower edge 120 has a plurality of openings 124. The plurality of openings 124 may be spaced along the lower edge 120 of the front wall 108. Both the ridge 122 and the plurality of openings 124 are configured to allow the commissural support 104 to removably attach to the mouthguard tray 102.

In some embodiments, the oral commissural splint 100 comprises more than one commissural support 104, as shown in FIGS. 4-7. For example, the oral commissural splint 100 may comprise two commissural supports 104 or at least one commissural support 104. Each commissural support 104 of the oral commissural splint 100 is configured to securely couple to the mouthguard tray 102. In some embodiments, the commissural support 104 has a clip 126 and a body 128 extending away from the clip 126. The body 128 may be integral with the clip 126, with the body 128 and the clip 126 formed of a single, unitary piece. The clip 126 may have a lip 130 that is configured to engage the ridge 122 of the mouthguard tray 102. The lip 130 helps to hold the commissural support 104 to the mouthguard tray 102 by hooking onto the ridge 122 or otherwise engaging or coupling with the ridge 122. The clip 126 may also have at least one clip arm 132. The at least one clip arm 132 is configured to engage with the plurality of openings 124 of the mouthguard tray 102 to hold the commissural support 104 to the mouthguard tray 102. In some embodiments, the at least one clip arm 132 has a clip projection 134 configured to insert into each of the plurality of openings 124. When the clip 126 is being coupled to the mouthguard tray 102, the lip 130 of the clip 126 may be placed over the ridge 122 of the mouthguard tray 102 and then the at least one clip arm 132 may be inserted into one or more of the plurality of openings 124 to prevent the lip 130 from lifting off of the ridge 122. In some embodiments, the clip projection 134 is configured to snap into each of the plurality of openings 124 to securely attach the commissural support 104 to the mouthguard tray 102. In this way, the lip 130 of the clip 126 and the ridge 122 of the mouthguard tray 102 together are configured to hold the clip 126, and therefore the commissural support 104, to the mouthguard tray 102.

Figure 6:
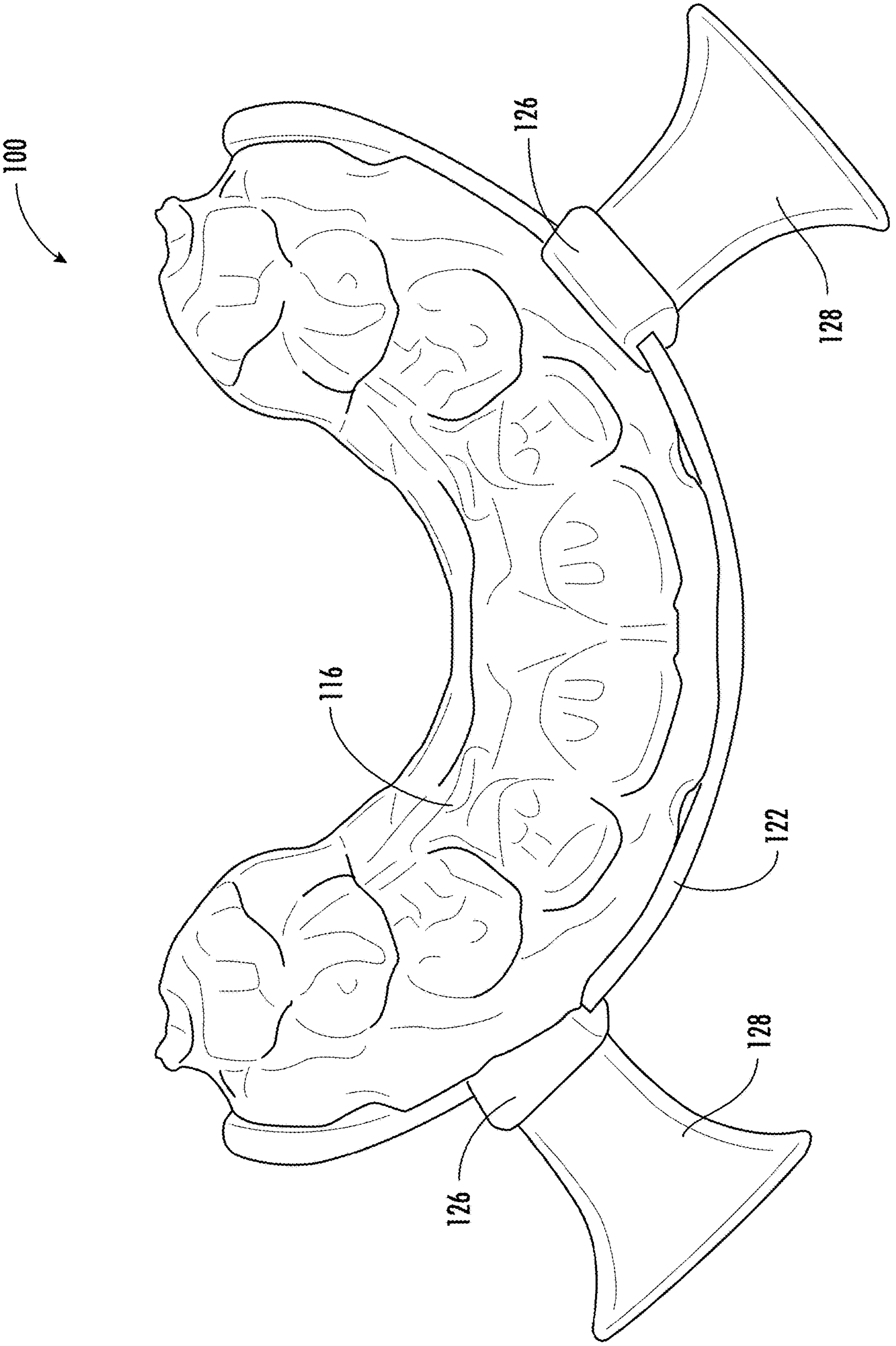
FIG. 6 is a top view of an oral commissural splint according to some embodiments with a mold retained in the mouthguard tray.

The body 128 of the commissural support 104 is configured for long-term support of a patient's commissure at the corner of the patient's mouth. This support is provided when the commissural support 104 is coupled to the mouthguard tray 102 and the mouthguard tray 102 is inserted into the patient's mouth and removably mounted on the patient's teeth. Because the mold 116 holds the mouthguard tray 102 in a fixed position with respect to the patient's teeth and the commissural support 104 is securely coupled to the mouthguard tray 102 as described above, the commissural support 104 can be positioned with respect to the mouthguard tray 102 to stretch the patient's commissure. Over the course of treatment, the commissural support 104 can be relocated to provide a progressively wider stretch to the patient. This process is quick and simple because the positions of each of the commissural supports 104 is adjustable, with the clip 126 of each commissural support 104 configured to removably snap into the desired position on the mouthguard tray 102 with the lip 130 of the clip 126 engaged with the ridge 122 of the mouthguard tray 102 and the clip projection 134 of the at least one clip arm 132 inserted into at least one of the plurality of openings 124. In some embodiments, a position of a first commissural support 104 with respect to the mouthguard tray 102 is independent of a position of a second commissural support 104 with respect to the 102. Because each commissural support 104 is independently movable with respect to the mouthguard tray 102, each commissure of the patient can be treated independently, according to the needs of the patient. This means that, in some embodiments, the first commissural support 104 and the second commissural support 104 are positionable such that the position of the first commissural support 104 is closer to a center of the mouthguard tray 102 than the position of the second commissural support 104, as shown in FIGS. 6 and 7. The opposite is also true, with the position of the first commissural support 104 closer to the center of the mouthguard tray 102 than the position of the second commissural support 104. Thus, positions of the commissural supports 104 are independent of each other, allowing for more flexible and targeted care directed towards the specific needs of each patient.

Many additional implementations are possible. Further implementations are within the CLAIMS.

It will be understood that implementations of the oral commissural splint include but are not limited to the specific components disclosed herein, as virtually any components consistent with the intended operation of various oral commissural splints may be utilized. Accordingly, for example, it should be understood that, while the drawings and accompanying text show and describe particular oral commissural splint implementations, any such implementation may comprise any shape, size, style, type, model, version, class, grade, measurement, concentration, material, weight, quantity, and/or the like consistent with the intended operation of oral commissural splints.

The concepts disclosed herein are not limited to the specific oral commissural splints shown herein. For example, it is specifically contemplated that the components included in particular oral commissural splints may be formed of any of many different types of materials or combinations that can readily be formed into shaped objects and that are consistent with the intended operation of oral commissural splints. For example, the components may be formed of: rubbers (synthetic and/or natural) and/or other like materials; glasses (such as fiberglass), carbon-fiber, aramid-fiber, any combination therefore, and/or other like materials; elastomers and/or other like materials; polymers such as thermoplastics (such as ABS, fluoropolymers, polyacetal, polyamide, polycarbonate, polyethylene, polysulfone, and/or the like, thermosets (such as epoxy, phenolic resin, polyimide, polyurethane, and/or the like), and/or other like materials; plastics and/or other like materials; composites and/or other like materials; metals, such as zinc, magnesium, titanium, copper, iron, steel, carbon steel, alloy steel, tool steel, stainless steel, spring steel, aluminum, and/or other like materials; and/or any combination of the foregoing.

Furthermore, oral commissural splints may be manufactured separately and then assembled together, or any or all of the components may be manufactured simultaneously and integrally joined with one another. Manufacture of these components separately or simultaneously, as understood by those of ordinary skill in the art, may involve 3-D printing, extrusion, pultrusion, vacuum forming, injection molding, blow molding, resin transfer molding, casting, forging, cold rolling, milling, drilling, reaming, turning, grinding, stamping, cutting, bending, welding, soldering, hardening, riveting, punching, plating, and/or the like. If any of the components are manufactured separately, they may then be coupled or removably coupled with one another in any manner, such as with adhesive, a weld, a fastener, any combination thereof, and/or the like for example, depending on, among other considerations, the particular material(s) forming the components.

In places where the description above refers to particular oral commissural splint implementations, it should be readily apparent that a number of modifications may be made without departing from the spirit thereof and that these implementations may be applied to other implementations disclosed or undisclosed. The presently disclosed oral commissural splints are, therefore, to be considered in all respects as illustrative and not restrictive.

I claim:

1. An oral commissural splint, comprising:
- a mouthguard tray configured to be inserted into a mouth of a patient and removably mounted on teeth of the patient, the mouthguard tray having:
  - a tooth platform having an upper surface with a plurality of textured structures on the upper surface;
  - a front wall extending up from the tooth platform and having an upper edge defining a ridge and a lower edge having a plurality of openings spaced along the lower edge of the front wall; and
  - a rear wall extending up from the tooth platform opposite the front wall; and
- two commissural supports configured to securely couple to the mouthguard tray, each of the two commissural supports having:
  - a clip having a lip configured to engage the ridge of the mouthguard tray and at least one clip arm having a clip projection configured to insert into each of the plurality of openings of the mouthguard tray, wherein the lip and the at least one clip arm together are configured to hold the clip to the mouthguard tray; and
  - a body integral with and extending away from the clip, the body configured for long-term support of a commissure at a corner of the mouth of the patient when the commissural support is coupled to the mouthguard tray and the mouthguard tray is inserted into the mouth of the patient and removably mounted on the teeth of the patient;
- wherein each clip of the two commissural supports is configured to removably snap into a desired position on the mouthguard tray with the lip engaged with the ridge of the mouthguard tray and the clip projection of the at least one clip arm inserted into at least one of the plurality of openings.

2. The oral commissural splint of claim 1, wherein a position of a first commissural support of the two commissural supports with respect to the mouthguard tray is independent of a position of a second commissural support of the two commissural supports with respect to the mouthguard tray.

3. The oral commissural splint of claim 2, wherein the first commissural support and the second commissural support are positionable such that the position of the first commissural support is closer to a center of the mouthguard tray than the position of the second commissural support.

4. The oral commissural splint of claim 1, wherein the plurality of textured structures are configured to mechanically engage a mold within the mouthguard tray, the mold formed of a dental impression material.

5. The oral commissural splint of claim 1, wherein positions of the two commissural supports with respect to the mouthguard tray are adjustable.

6. An oral commissural splint, comprising:

a mouthguard tray configured to be removably retained within a mouth of a patient through an opening in the mouth of the patient, the mouthguard tray having a front wall, the front wall having a plurality of openings spaced along a lower edge of the front wall; and at least one commissural support configured to securely couple to the mouthguard tray, the at least one commissural support having a clip with at least one clip arm configured to positionally hold the commissural support in relation to the mouthguard tray, and a body extending away from the clip, the body configured for long-term support of and contact with a commissure at a corner of the mouth of the patient when the at least one commissural support is coupled to the mouthguard tray and the mouthguard tray is inserted into the mouth of the patient, wherein the at least one commissural support is further configured to extend the commissure away from a center of the opening in the mouth of the patient, the front wall having an upper edge defining a ridge and the clip having a lip configured to engage the ridge, wherein the clip of the at least one commissural support is configured to removably snap into a desired position on the mouthguard tray with the lip engaged with the ridge of the mouthguard tray and the at least one clip arm inserted into at least one of the plurality of openings of the mouthguard tray.

7. The oral commissural splint of claim 6, wherein a position of a first commissural support of the at least one commissural support with respect to the mouthguard tray is independent of a position of a second commissural support of the at least one commissural support with respect to the mouthguard tray.

8. The oral commissural splint of claim 7, wherein the first commissural support and the second commissural support are positionable such that the position of the first commissural support is closer to a center of the mouthguard tray than the position of the second commissural support.

9. The oral commissural splint of claim 6, the mouthguard tray further having a tooth platform having an upper surface with a plurality of textured structures on the upper surface, wherein the front wall extends up from the tooth platform and wherein the plurality of textured structures are configured to mechanically engage a mold within the mouthguard tray, the mold formed of a dental impression material.

10. The oral commissural splint of claim 6, wherein the at least one clip arm has a clip projection configured to insert into each of the plurality of openings.

11. The oral commissural splint of claim 6, wherein the body is integral with the clip.

12. An oral commissural splint, comprising:

a mouthguard tray configured to be removably retained within a mouth of a patient through an opening in the mouth of the patient; and at least one commissural support configured to movably couple to the mouthguard tray with the at least one commissural support movable between desired spatial positions in relation to the mouthguard tray, wherein the at least one commissural support remains in each of the desired spatial positions when placed there to support and contact a commissure at a corner of the mouth of the patient when the mouthguard tray is inserted into the mouth of the patient over an extended period of time exceeding a day, wherein the at least one commissural support is further configured to extend the commissure away from a center of the opening in the mouth of the patient, the mouthguard tray having a front wall, the front wall having a plurality of openings spaced along the front wall, the at least one commissural support having a clip with at least one clip arm configured to hold the clip to the mouthguard tray and a body extending away from the clip, the body configured to support the commissure at the corner of the mouth of the patient when the mouthguard tray is inserted into the mouth of the patient, the front wall having an upper edge defining a ridge and the clip having a lip configured to engage the ridge, wherein the clip of the at least one commissural support is configured to removably snap into the desired spatial position on the mouthguard tray with the lip engaged with the ridge of the mouthguard tray and the at least one clip arm inserted into at least one of the plurality of openings of the mouthguard tray.

13. The oral commissural splint of claim 12, wherein a position of a first commissural support of the at least one commissural support with respect to the mouthguard tray is independent of a position of a second commissural support of the at least one commissural support with respect to the mouthguard tray.

14. The oral commissural splint of claim 13, wherein the first commissural support and the second commissural support are positionable such that the position of the first commissural support is closer to a center of the mouthguard tray than the position of the second commissural support.

15. The oral commissural splint of claim 12, wherein the body is integral with the clip.

16. The oral commissural splint of claim 12, the mouthguard tray further having a tooth platform having an upper surface with a plurality of textured structures on the upper surface, wherein the plurality of textured structures are configured to mechanically engage a mold within the mouthguard tray, the mold formed of a dental impression material.

17. The oral commissural splint of claim 12, wherein a position of the at least one commissural support with respect to the mouthguard tray is adjustable.

18. The oral commissural splint of claim 12, wherein the at least one clip arm has a clip projection configured to insert into each of the plurality of openings.

* * * * *